US008118884B2

(12) United States Patent
Ascione et al.

(10) Patent No.: US 8,118,884 B2
(45) Date of Patent: Feb. 21, 2012

(54) DYEING OR LIGHTENING COMPOSITIONS COMPRISING AT LEAST ONE FATTY SUBSTANCE AND AT LEAST ONE AMPHOTERIC POLYMER

(75) Inventors: Jean-Marc Ascione, Paris (FR); Jean Cotteret, Maisons Laffite (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/976,124

(22) Filed: Dec. 22, 2010

(65) Prior Publication Data

US 2011/0158925 A1    Jun. 30, 2011

Related U.S. Application Data

(60) Provisional application No. 61/294,931, filed on Jan. 14, 2010.

(30) Foreign Application Priority Data

Dec. 22, 2009 (FR) ...................... 09 59391

(51) Int. Cl.
*A61Q 5/10* (2006.01)
(52) U.S. Cl. ............. 8/405; 8/406; 8/410; 8/421; 8/435; 8/552; 8/557; 8/558; 8/559; 8/580; 8/604
(58) Field of Classification Search .............. 8/405, 406, 8/410, 421, 435, 552, 557, 558, 559, 580, 8/604
See application file for complete search history.

(56) References Cited

U.S. PATENT DOCUMENTS

| | | |
|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2003/0064494 A1 | 4/2003 | Kumar et al. |
| 2003/0190297 A1 | 10/2003 | Narasimhan et al. |

(Continued)

FOREIGN PATENT DOCUMENTS

CA        1 268 421        5/1990

(Continued)

OTHER PUBLICATIONS

European Search Report for EP 10 19 5262, dated Apr. 1, 2011.
P.R. Canterbery et al., International Cosmetic Ingredient Dictionary and Handbook, vol. 1, p. 759 (2002).
Ullmann's Encyclopedia of Industrial Chemistry, "Hair Preparations," Wiley-VCH Verlag GnbH & Co., KGaA, Weinheim, p. 20 (2006).
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.

(Continued)

*Primary Examiner* — Eisa Elhilo

(74) *Attorney, Agent, or Firm* — Finnegan, Henderson, Farabow, Garrett & Dunner, LLP

(57) ABSTRACT

The subject of the present disclosure relates to compositions for dyeing or lightening human keratin fibers, comprising: (a) at least 25% by weight of at least one fatty substance; (b) at least one amphoteric polymer; (c) at least one basifying agent; and (d) at least one oxidizing agent. The present disclosure also relates to a dyeing or lightening processes using the composition, and two- and three-compartment devices which make it possible to obtain a composition according to the present disclosure, after mixing of the compositions of the compartments just before application of the composition according to the present disclosure.

31 Claims, No Drawings

U.S. PATENT DOCUMENTS

| | | |
|---|---|---|
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0221400 A1 | 11/2004 | Cotteret et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand ............................ 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 449 512 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |

| | | |
|---|---|---|
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,150, filed Dec. 22, 2010.
Copending U.S. Appl. No. 12/976,173, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.

French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
International Search Report for PCT/FR2009/052617, dated Mar. 30, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Mar. 16, 2011, in co-pending U.S. Appl. No. 12/642,583.
Office Action mailed Mar. 29, 2011, in co-pending U.S. Appl. No. 12/642,468.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

DYEING OR LIGHTENING COMPOSITIONS COMPRISING AT LEAST ONE FATTY SUBSTANCE AND AT LEAST ONE AMPHOTERIC POLYMER

This application claims benefit of U.S. Provisional Application No. 61/294,931, filed Jan. 14, 2010. This application also claims benefit of priority under 35 U.S.C. §119 to French Patent Application No. 0959391, filed Dec. 22, 2009.

The present disclosure relates to compositions for dyeing or lightening human keratin fibers in the form of a water-in-oil emulsion, for example an emulsion with a continuous oily phase wherein the dispersed phase is water.

Among the methods for dyeing human keratin fibers, such as the hair, oxidation dyeing or permanent dyeing is known in the art. For example, this dyeing method uses at least one oxidation dye, and at least one oxidation base optionally combined with at least one coupler.

For instance, oxidation bases are chosen from ortho- or para-phenylenediamines, ortho- or para-aminophenols and heterocyclic compounds. These oxidation bases are colorless or weakly colored compounds which, when combined with oxidizing products, can give access to colored species.

The shades obtained with these oxidation bases are often varied by combining them with at least one coupler, the latter being chosen, for example, from aromatic meta-diamines, meta-aminophenols, meta-diphenols and certain heterocyclic compounds, such as indole compounds.

The variety of molecules used as oxidation bases and couplers can enable a wide range of colors to be obtained.

Direct dyeing or semi-permanent dyeing is also known in the art. The process conventionally used in direct dyeing comprises applying direct dyes to the keratin fibers, wherein the direct dyes are colored and have an affinity for the fibers. The direct dyes are left on the keratin fibers and then rinsed out.

Exemplary direct dyes include, but are not limited it nitrobenzene, anthraquinone, nitropyridine, azo, methine, azomethine, xanthene, acridine, azine and triarylmethane direct dyes.

Direct dyeing does not require the use of an oxidizing agent in order to develop the dyeing, although an oxidizing agent can be used in the direct dyeing process order to obtain a lightening effect. This process is referred to as direct or semi-permanent dyeing under lightening conditions.

Permanent and semi-permanent dyeing processes under lightening conditions therefore consist in using, with the dye composition, an aqueous composition comprising at least one oxidizing agent, under alkaline pH conditions in the vast majority of cases. The role of this oxidizing agent is, for example, to degrade the melanin in the hair, which, depending on the nature of the oxidizing agent present, may result in a pronounced lightening of the fibers. For a relatively low degree of lightening, the oxidizing agent is for example hydrogen peroxide. When a greater degree of lightening is required, peroxygenated salts, such as persulphates may be used, in the presence of hydrogen peroxide.

There is a need in the art for effective lightening and dyeing products, such as in terms of lightening power or of dyeing strength and/or of selectivity, while lessening the harmful effects associated with the simultaneous presence of alkaline agents and oxidizing agents such as hydrogen peroxide, for example lessening the degradation of keratin fibers and reducing the unpleasantness associated with the odor of the alkaline agents used, such as aqueous ammonia and amines.

The compositions according to the present disclosure may increase the effects of the alkaline agents and/or of the oxidizing agents while at the same time have maximum dyeing or lightening effectiveness on keratin fibers.

The present disclosure therefore relates to compositions for dyeing or lightening human keratin fibers, comprising:
 a) at least 25% by weight of at least one fatty substance not comprising a carboxylic acid functional group;
 b) at least one amphoteric polymer;
 c) at least one basifying agent; and
 d) hydrogen peroxide.

Another aspect of the present disclosure relates to a process for treating human keratin fibers, such as the hair, using this composition.

When compositions in accordance with the present disclosure are intended for dyeing keratin fibers, the compositions may further comprise at least one oxidation dye and/or at least one direct dye.

Conversely, when compositions according to the present disclosure are intended solely for bleaching keratin fibers, the compositions may not comprise a direct dye or an oxidation dye (bases and couplers) or in the alternative, if they are present, their total content does not exceed 0.005% by weight relative to the weight of the composition such that only the composition would be colored, i.e. no dyeing effect would be observed on the keratin fibers.

Another aspect of the present disclosure is a two-compartment device comprising, in one compartment, a first composition comprising at least one fatty substance not comprising a carboxylic acid functional group, at least one basifying agent, and optionally at least one dye chosen from oxidation dyes and direct dyes; and in the other compartment, a second composition comprising hydrogen peroxide; and wherein the first and/or the second composition further comprise at least one amphoteric polymer.

Yet another aspect of the present disclosure relates to a three-compartment device comprising, in one compartment, a composition comprising at least one fatty substance not comprising a carboxylic acid functional group; in another compartment, a composition comprising at least one basifying agent and, optionally, at least one dye chosen from oxidation dyes and direct dyes; and in the final compartment, a composition comprising hydrogen peroxide; wherein at least one of these compositions further comprises at least one amphoteric polymer.

The compositions of the various devices according to the present disclosure may be mixed to give the compositions disclosed herein just before application to the human keratin fibers.

Other characteristics and benefits of the present disclosure will emerge more clearly on reading the description and the examples which follow.

In the text hereinbelow, unless otherwise indicated, the limits of a range of values are included in that range.

The compositions according to the present disclosure comprise at least 25% by weight of at least one fatty substance not comprising a carboxylic functional group.

As used herein, "fatty substance" is understood to mean an organic compound that is insoluble in water at ordinary temperature (25° C.) and at atmospheric pressure (760 mmHg; i.e. $1.013 \times 10^5$ Pa) (solubility of less than 5%, such as less than 1%, for example less than 0.1%). They have in their structure at least one hydrocarbon-based chain comprising at least 6 carbon atoms or a sequence of at least two siloxane groups. In addition, the at least one fatty substance is soluble in organic solvents under the same temperature and pressure conditions, for instance chloroform, ethanol or benzene.

As used herein, "fatty substance not comprising a carboxylic acid functional group" is understood to mean a fatty substance not comprising a —COOH group or a —COO— group.

According to the present disclosure, the at least one fatty substance is chosen from compounds that are liquid or pasty at ambient temperature and at atmospheric pressure.

For example, the at least one fatty substance can be chosen from $C_6$-$C_{16}$ lower alkanes; non-silicone oils of animal, plant and synthetic origin; hydrocarbons of mineral and synthetic origin; fatty alcohols; fatty acid esters; fatty alcohol esters; non-silicone waxes; and silicones.

The $C_6$-$C_{16}$ lower alkanes that may be mentioned, in a non-limiting manner, include linear or branched, or optionally cyclic alkanes, such as hexane, undecane, dodecane, tridecane and isoparaffins such as isohexadecane and isodecane.

Suitable oils of animal, plant or synthetic origin that may be used in accordance with the present disclosure include, but are not limited to:

hydrocarbon-based oils of animal origin, such as perhydrosqualene;

triglyceride oils of plant or synthetic origin, such as liquid fatty acid triglycerides comprising from 6 to 30 carbon atoms, for instance heptanoic and octanoic acid triglycerides; sunflower oil; corn oil; soybean oil; marrow oil; grapeseed oil; sesame seed oil; hazelnut oil; apricot oil; macadamia oil; arara oil; castor oil; avocado oil; caprylic/capric acid triglycerides, for instance those sold by the company Stéarineries Dubois or those sold under the names MIGLYOL® 810, 812 and 818 by the company Dynamit Nobel; jojoba oil and shea butter oil;

linear and branched hydrocarbons of mineral and synthetic origin, comprising more than 16 carbon atoms, such as volatile and non-volatile liquid paraffins, and derivatives thereof; petroleum jelly; liquid petroleum jelly; polydecenes; and hydrogenated polyisobutene such as PARLEAM®; and fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, and bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

In accordance with the present disclosure, the fatty alcohols, fatty acid esters, and fatty alcohol esters may comprise, for example, at least one linear or branched, saturated or unsaturated hydrocarbon-based group comprising 6 to 30 carbon atoms, which may be optionally substituted, for instance with at least one hydroxyl group, and in at least one embodiment, substituted with 1 to 4 hydroxyl groups. If they are unsaturated, these compounds may further comprise one to three conjugated or non-conjugated carbon-carbon double bonds.

Suitable fatty alcohols include, but are not limited to linear and branched, saturated and unsaturated alcohols comprising 8 to 30 carbon atoms, such as cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

Non-limiting examples of fatty acid esters and fatty alcohol esters, which are different from the triglycerides mentioned above, include esters of saturated and unsaturated, linear and branched $C_1$-$C_{26}$ aliphatic mono and polyacids, and of saturated and unsaturated, linear and branched $C_1$-$C_{26}$ aliphatic mono- and polyalcohols, wherein the total carbon number of the esters is greater than or equal to 10.

Among the monoesters, mention may be made, in a non-limiting manner, of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl and stearyl myristate; hexyl stearate; butyl stearate; isobutyl stearate; dioctyl malate; hexyl laurate; and 2-hexyldecyl laurate.

Other suitable examples include esters of $C_4$-$C_{22}$ dicarboxylic and tricarboxylic acids and of $C_1$-$C_{22}$ alcohols and esters of mono-, di- and tricarboxylic acids and of $C_2$-$C_{26}$ di-, tri-, tetra- or pentahydroxy alcohols.

According to at least one embodiment of the present disclosure, the at least one fatty substance may be chosen from diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, ethyl, isopropyl, myristyl, cetyl and stearyl palmitate, 2-ethylhexyl palmitate, 2-octyldecyl palmitate, alkyl myristates such as isopropyl, butyl, cetyl and 2-octyldodecyl myristate, hexyl stearate, butyl stearate, isobutyl stearate; dioctyl malate, hexyl laurate, 2-hexyldecyl laurate, isononyl isononanoate and cetyl octanoate, may be used according to the present disclosure.

The compositions may also comprise, as a non-limiting example of fatty esters, sugar esters and diesters of $C_6$-$C_{30}$ such as $C_{12}$-$C_{22}$ fatty acids. As used herein, "sugar" is understood to mean an oxygen-bearing hydrocarbon-based compound comprising several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, for example alkyl derivatives, such as methyl derivatives, for instance methylglucose.

Non-limiting examples of sugar esters of fatty acids include, but are not limited to linear and branched, saturated and unsaturated $C_6$-$C_{30}$ fatty acids, such as $C_{12}$-$C_{22}$ fatty acids, and mixtures thereof. If they are unsaturated, these compounds may further comprise one to three conjugated or non-conjugated carbon-carbon double bonds.

Other suitable esters include mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as oleopalmitate, oleostearate and palmito-stearate mixed esters.

According to at least one embodiment, monoesters and diesters, such as sucrose, glucose and methylglucose mono- and dioleates, stearates, behenates, oleopalmitates, linoleates, linolenates and oleostearates, may be used.

For example, mention may be made in a non-limiting manner of the product sold under the name GLUCATE® DO by the company Amerchol, which is a methylglucose dioleate.

Other useful examples of esters or mixtures of esters of sugar and of fatty acids that may be mentioned include:

the products sold under the names F160, F140, F110, F90, F70 and SL40 by the company Crodesta, which comprise sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% di-triester-polyester;

the sucrose mono-dipalmito-stearate sold by the company Goldschmidt under the name TEGOSOFT® PSE.

According to the present disclosure, examples of non-silicone waxes that may be included in the compositions herein are chosen, for example, from carnauba wax; candelilla wax; esparto grass wax; paraffin wax; ozokerite; plant waxes; for instance olive wax, rice wax, hydrogenated jojoba wax; the absolute waxes of flowers such as the essential wax of blackcurrant flower sold by the company Bertin (France); animal waxes, for instance beeswaxes, and modified beeswaxes (cerabellina); waxy raw materials such as marine waxes, for example the product sold by the company Sophim under the reference M82; and waxes of polyethylene and of polyolefins.

The silicones that may be used in the cosmetic compositions of the present disclosure are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^{-5}$ to 1 m$^2$/s.

The silicones that may be used according to the present disclosure may be chosen from oils, waxes, resins and gums.

In at least one embodiment, the silicone is chosen from polydialkylsiloxanes, for instance polydimethylsiloxanes (PDMS), and organomodified polysiloxanes comprising at least one functional group chosen from poly(oxyalkylene) groups, amino groups and alkoxy groups.

The organopolysiloxanes are defined for example in Walter Noll's "Chemistry and Technology of Silicones" (1968) Academic Press. They can be volatile or non-volatile.

When they are volatile, the silicones are for instance chosen from those having a boiling point ranging from 60° C. to 260° C., such as:

(i) cyclic polydialkylsiloxanes comprising 3 to 7 silicon atoms, for instance, comprising 4 to 5 silicon atoms. These are, for example, octamethylcyclotetrasiloxane sold under the name VOLATILE SILICONE® 7207 by Union Carbide or Silbione® 70045 V2 by Rhodia, decamethylcyclopentasiloxane sold under the name VOLATILE SILICONE® 7158 by Union Carbide, and Silbione® 70045 V5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

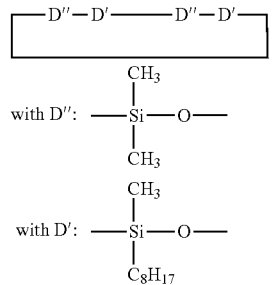

Mention may also be made, in a non-limiting manner, of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2, 2,2',2',3,3'-hexatrimethylsilyloxy)neopentane;

(ii) linear volatile polydialkylsiloxanes comprising 2 to 9 silicon atoms and having a viscosity of less than or equal to $5 \times 10^{-6}$ m$^2$/s at 25° C. An example is decamethyltetrasiloxane sold under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Non-volatile polydialkylsiloxanes, polydialkylsiloxane gums and resins, polyorganosiloxanes modified with organofunctional groups above, and mixtures thereof, may also be used.

These silicones are, in at least one embodiment, chosen from polydialkylsiloxanes, among which non-limiting mention may be made of polydimethylsiloxanes comprising trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60,000 mm$^2$/s;

the VISCASIL® oils from General Electric and certain oils of the SF series (SF 96, SF 18) from General Electric.

Mention may also be made of polydimethylsiloxanes comprising dimethylsilanol end groups known under the name Dimethiconol (CTFA), such as the oils of the 48 series from the company Rhodia.

In this category of polydialkylsiloxanes, non-limiting mention may also be made of the products sold under the names ABIL WAX® 9800 and 9801 by the company Goldschmidt, which are poly($C_1$-$C_{20}$)dialkylsiloxanes.

The silicone gums that can be used in accordance with the disclosure include, but are not limited to polydialkylsiloxanes, such as polydimethylsiloxanes with high number-average molecular masses ranging from 200,000 to 1,000,000, alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

According to at least one embodiment of the present disclosure, products that can be used are mixtures chosen from:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, such as a PDMS gum and a PDMS oil, for example the product SF 1236 from the company General Electric. The product SF 1236 is the mixture of an SE 30 gum defined above, having a viscosity of 20 m$^2$/s, and an SF 96 oil, with a viscosity of $5 \times 10^{-6}$ m$^2$/s. This product for instance comprises 15% SE 30 gum and 85% SF 96 oil.

Other suitable organopolysiloxane resins that can be used in accordance with the present disclosure are crosslinked siloxane systems comprising the following units:

$R_2SiO_{2/2}$, $R_3SiO_{1/2}$, $RSiO_{3/2}$ and $SiO_{4/2}$ wherein R is chosen from $C_1$-$C_{16}$ alkyl groups, such as $C_1$-$C_4$ lower alkyl groups, for example, methyl.

Among these resins, non-limiting mention may be made of the product sold under the name DOW CORNING 593 or those sold under the names SILICONE FLUID SS 4230 and SS 4267 by the company General Electric, which are silicones of dimethyl/trimethyl siloxane structure.

Mention may also be made of the trimethyl siloxysilicate type resins sold for instance under the names X22-4914, X21-5034 and X21-5037 by the company Shin-Etsu.

The organomodified silicones that can be used in accordance with the present disclosure include, but are not limited to silicones as defined above and comprising in their structure at least one organofunctional groups attached via a hydrocarbon-based group.

In at least one embodiment, the organomodified silicones may be chosen from polydiarylsiloxanes, such as polydiphenylsiloxanes, and polyalkylarylsiloxanes functionalized with the organofunctional groups mentioned previously.

For example, the polyalkylarylsiloxanes are chosen from linear and branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, non-limiting examples include the products sold under the following names:

the SILBIONE® oils of the 70 641 series from Rhodia;

the oils of the RHODORSIL® 70 633 and 763 series from Rhodia;

the oil DOW CORNING 556 Cosmetic Grade Fluid from Dow Corning;

the silicones of the PK series from Bayer, such as the product PK20;

the silicones of the PN and PH series from Bayer, such as the products PN1000 and PH1000; and certain oils of the SF series from General Electric, such as SF 1023, SF 1154, SF 1250 and SF 1265.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups; and alkoxylated groups such as the product sold under the name SILICONE COPOLYMER F-755 by SWS Silicones, and ABIL WAX® 2428, 2434 and 2440 by the company Goldschmidt.

In accordance with the present disclosure, the at least one fatty substance is chosen from compounds that are liquid or pasty at ambient temperature and at atmospheric pressure, such as liquid.

For example, the at least one fatty substance is chosen, for instance, from $C_6$-$C_{16}$ lower alkanes; fatty alcohols; fatty acid esters; fatty alcohol esters; oils such as mineral, plant and synthetic non-silicone oils; and silicones.

In at least one embodiment, the at least one fatty substance is chosen from liquid petroleum jelly, polydecenes, liquid esters of fatty acids and/or fatty alcohols, liquid fatty alcohols, and mixtures thereof.

The compositions according to the present disclosure comprise at least 25% by weight of at least one fatty substance. For example, the amount of the at least one fatty substance ranges from 25% to 80% by weight, such as from 25% to 65% by weight, for instance from 30% to 55% by weight, relative to the weight of the composition.

The compositions according to the present disclosure compriss at least one amphoteric polymers.

The amphoteric (or zwitterionic) polymers that can be used in accordance with the present disclosure can be chosen from polymers comprising B and C units distributed randomly in the polymer chain, wherein B is chosen from units derived from a monomer comprising at least one basic nitrogen atom and C is chosen from units derived from an acid monomer comprising at least one carboxylic or sulphonic groups, or in the alternative B and C are chosen from groups derived from carboxybetaine and sulphobetaine zwitterionic monomers; B and C may also be a cationic polymer chain comprising primary, secondary, tertiary or quaternary amine groups, wherein at least one of the amine groups bears a carboxylic or sulphonic group linked via a hydrocarbon-based radical or in the alternative B and C form part of a chain of a polymer comprising an α,β-dicarboxylic ethylene unit wherein one of the carboxylic groups has been made to react with a polyamine comprising at least one primary or secondary amine groups. Non-limiting examples of the at least one amphoteric polymer corresponding to the definition given above include, but are not limited to:

1) polymers comprising, as monomers, at least one monomer derived from a vinyl compound bearing a carboxylic group, such as acrylic acid, methacrylic acid, maleic acid, and α-chloroacrylic acid, and at least one basic monomer derived from a substituted vinyl compound comprising at least one basic atom, chosen for example from:

a) dialkyl aminoalkyl methacrylates, dialkyl aminoalkyl acrylates, dialkyl aminoalkyl methacrylamides and dialkyl aminoalkyl acrylamides. Such compounds are described, for instance, in U.S. Pat. No. 3,836,537;

b) salts of trialkyl aminoalkyl methacrylates and of trialkyl aminoalkyl acrylates, salts of trialkylaminoalkylmethacrylamide and of trialkylaminoalkylacrylamide. Mention may be made of the acrylic acid/acrylamidopropyltrimethylammonium chloride copolymer proposed by the company Stockhausen under the name POLYMER W3794. Mention may also be made, in a non-limiting manner, of the acrylic acid/acrylamidopropyltrimethylammonium chloride/acrylamide copolymers proposed by the company Nalco under the name MERQUAT 2001 and MERQUAT 2003;

(2) polymers comprising units deriving from:

a) at least one monomer chosen from acrylamides or methacrylamides which are substituted on the nitrogen with an alkyl radical, b) at least one acidic comonomer comprising at least one reactive carboxylic group, and c) at least one basic comonomer such as esters comprising primary, secondary, tertiary and quaternary amine substituents of acrylic and methacrylic acids and the product of quaternization of dimethylaminoethyl methacrylate with dimethyl sulphate or diethyl sulphate.

Suitable N-substituted acrylamides and methacrylamides that may be used according to the present disclosure include groups wherein the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen for example from acrylic acid, methacrylic acid, crotonic acid, itaconic acid, maleic acid and fumaric acid and $C_1$-$C_4$ alkyl monoesters of maleic and fumaric acids and anhydrides.

Suitable basic comonomers include, but are not limited to aminoethyl, butylaminoethyl, N,N'-dimethylaminoethyl and N-tert-butylaminoethyl methacrylates, for example, the copolymers of which the CTFA name (4th Edition, 1991) is octylacrylamide/acrylates/butylaminoethyl methacrylate copolymer, such as the products sold under the name AMPHOMER or LOVOCRYL 47 by the company National Starch;

(3) copolymers comprising, as monomers, at least one monomer derived from a vinyl compound bearing a carboxylic group, such as acrylic acid, methacrylic acid, maleic acid or α-chloroacrylic acid, and at least one monomer of diallyl dialkyl ammonium salt type, wherein the alkyl groups comprise 1 to 6 carbon atoms such as methyl.

Among these polymers, the copolymers comprising, as monomers, dimethyldiallylammonium chloride and acrylic acid, optionally combined with acrylamide, are used in at least one embodiment. Non-limiting mention may be made of the compounds proposed by the company Nalco under the names MERQUAT 280, MERQUAT 295, MERQUAT 3330, MERQUAT 3331 and MERQUAT 3333;

(4) crosslinked and alkylated polyamino amides partially or totally derived from polyamino amides of formula (I):

$$-[CO-R_{10}-CO-Z]- \quad (I)$$

wherein $R_{10}$ is chosen from divalent radicals derived from a saturated dicarboxylic acid, a mono- or dicarboxylic aliphatic acid comprising an ethylenic double bond, an ester of a lower alkanol, having 1 to 6 carbon atoms, and radicals derived from the addition of any one of said acids to a bis (primary) or bis(secondary) amine, and Z is chosen from radicals of a bis(primary), mono- and bis(secondary) polyalkylene-polyamine such as:

a) in an amount ranging from 60 to 100 mol %, the radical:

$$-\underset{H}{N}-[(CH_2)_x-\underset{H}{N}-]_p \quad (II)$$

wherein x=2 and p=2 or 3, or in the alternative x=3 and p=2 this radical deriving from diethylenetriamine, from triethylenetetraamine or from dipropylenetriamine;

b) in an amount ranging from 0 to 40 mol %, the radical (II) above wherein x=2 and p=1 and which derives from ethylenediamine, or the radical derived from piperazine:

$$-N\diagdown\diagup N-$$

c) in an amount ranging from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide, and alkylated by the action of acrylic acid, chloroacetic acid or an alkane sultone, or salts thereof.

The saturated carboxylic acids are for instance chosen from acids having 6 to 10 carbon atoms, such as adipic acid, 2,2,4-trimethyl adipic acid and 2,4,4-trimethyl adipic, terephthalic acid, acids comprising an ethylenic double bond such as acrylic acid, methacrylic acid and itaconic acid.

The alkane sultones used in the alkylation are for example propane sultone and butane sultone, the salts of the alkylating agents are for instance the sodium or potassium salts;

(5) polymers comprising zwitterionic units of formula:

$$R_{11}-\left[\underset{R_{13}}{\overset{R_{12}}{\underset{|}{\overset{|}{C}}}}\right]_y-\underset{R_{15}}{\overset{R_{14}}{\underset{|}{\overset{|}{N^+}}}}-(CH_2)_z-\overset{O}{\underset{}{\overset{\|}{C}}}-O^- \quad (III)$$

wherein $R_{11}$ is chosen from polymerizable unsaturated groups such as acrylate, methacrylate, acrylamide and methacrylamide group, y and z are integers ranging from 1 to 3, $R_{12}$ and $R_{13}$ are each independently chosen from a hydrogen atom, methyl, ethyl and propyl, $R_{14}$ and $R_{15}$ are each independently chosen from a hydrogen atom and alkyl radicals such that the sum of the carbon atoms in $R_{14}$ and $R_{15}$ does not exceed 10.

The polymers comprising such units can also comprise units derived from nonzwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the methyl methacrylate/methyl dimethylcarboxymethylammonioethylmethacrylate copolymer, such as the product sold under the name DIAFORMER Z301 by the company Sandoz;

(6) polymers derived from chitosan comprising monomer units chosen from those of formulae (D)-(F):

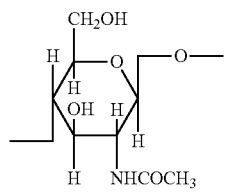

(D)

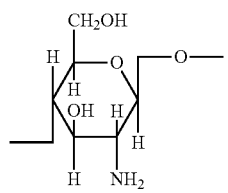

(E)

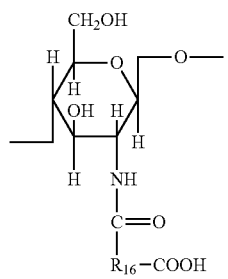

(F)

wherein the D unit is present in proportions ranging from 0% to 30%, the E unit is present in proportions ranging from 5% to 50% and the F unit is present in proportions ranging from 30% and to 90%, it being understood that, in the F unit, $R_{16}$ is a radical of formula:

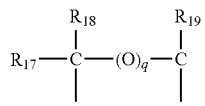

wherein, if q=0, $R_{17}$, $R_{18}$ and $R_{19}$, are each independently chosen from a hydrogen atom, methyl, hydroxyl, acetoxy, amino, monoalkylamine, and dialkylamine, which is optionally interrupted with at least one nitrogen atom and/or optionally substituted with at least one group chosen from amine, hydroxyl, carboxyl, alkylthio and sulphonic groups, alkylthio wherein the alkyl group bears an amino residue, wherein at least one of the radicals $R_{17}$, $R_{18}$ and $R_{19}$ is a hydrogen atom;

or, if q=1, $R_{17}$, $R_{18}$ and $R_{19}$ each represent a hydrogen atom, and also the salts formed by these compounds with bases or acids;

(7) polymers derived from the N-carboxyalkylation of chitosan, such as the N-carboxymethyl chitosan or the N-carboxybutyl chitosan sold under the name EVALSAN by the company Jan Dekker;

(8) polymers having units chosen from those of formula (IV), which are disclosed in French Patent No. 1 400 366:

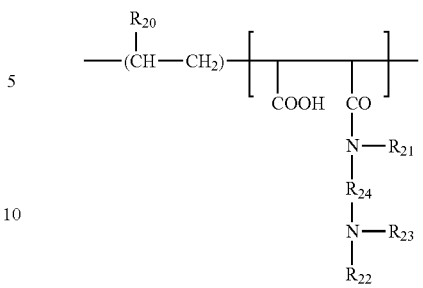

(IV)

wherein $R_{20}$ is chosen from a hydrogen atom, $CH_3O$, $CH_3CH_2O$, and phenyl, $R_{21}$ is chosen from a hydrogen atom, lower alkyl radicals such as methyl or ethyl, $R_{23}$ is chosen from a lower alkyl radical such as methyl or ethyl or a radical chosen from formula: $-R_{24}-N(R_{22})_2$, wherein $R_{24}$ is chosen from $-CH_2-CH_2-$, $-CH_2-CH_2-CH_2-$ and $-CH_2-CH(CH_3)-$, $R_{22}$ is chosen from a hydrogen atom and a lower alkyl radical such as methyl or ethyl, and also the higher homologues of these radicals, comprising up to 6 carbon atoms;

(9) amphoteric polymers of the -D-X-D-X type chosen from:

a) polymers obtained by the action of chloroacetic acid or sodium chloroacetate on compounds comprising at least one unit of formula (V):

-D-X-D-X-D- (V)

wherein D is a radical

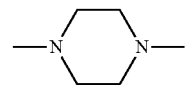

and X is the symbol E or E', which are independently chosen from alkylene radicals with a straight or branched chain comprising up to 7 carbon atoms in the main chain, which is unsubstituted or substituted with hydroxyl groups and which can comprise, in addition to the oxygen, nitrogen and sulphur atoms, 1 to 3 aromatic and/or heterocyclic rings; wherein the oxygen, nitrogen and sulphur atoms are present in the form of ether, thioether, sulphoxide, sulphone, sulphonium, alkylamine, or alkenylamine groups, or hydroxyl, benzylamine, amine oxide, quaternary ammonium, amide, imide, alcohol, ester and/or urethane groups;

b) polymers of formula (VI):

-D-X-D-X— (VI)

where D denotes a radical

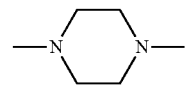

and X denotes the symbol E or E' and at least once E'; E has the meaning indicated above and E' is chosen from alkylene radicals with a straight or branched chain having up to 7 carbon atoms in the main chain, which is unsubstituted or substituted with at least one hydroxyl radicals, and comprising at least one nitrogen atoms, the nitrogen atom being substituted with an alkyl chain optionally interrupted with an oxygen atom and necessarily comprising at least one carboxyl functional group or at least one hydroxyl functional group and betainized by reaction with chloroacetic acid or sodium chloroacetate;

(10) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

According to at least one embodiment, the at least one amphoteric polymer is chosen from the compounds of groups (1) and (3) discussed above, such as the compounds of group (1), for example the acrylic acid/acrylamidopropyltrimethylammonium chloride copolymer.

In the compositions of the present disclosure, the at least one amphoteric polymer is present in an amount ranging from 0.005% to 10%, such as from 0.05% to 5%, for example from 0.1% to 2% by weight, relative to the total weight of the composition.

The compositions disclosed herein comprise at least one basifying agent chosen from inorganic and organic alkaline agents and hybrids and mixtures thereof.

In at least one embodiment, the at least one inorganic alkaline agent is chosen from aqueous ammonia, alkali metal carbonates and bicarbonates, such as sodium and potassium carbonates, sodium and potassium bicarbonates, sodium hydroxide and potassium hydroxide, and mixtures thereof.

In at least one embodiment, the at least one organic alkaline agent is chosen from organic amines with a pKb at 25° C. of less than 12, such as less than 10, for instance less than 6. It should be noted that this is the pKb corresponding to the function of highest basicity.

By way of hybrid compounds, mention may be made of the salts of the abovementioned amines with acids such as carbonic acid or hydrochloric acid.

The at least one organic alkaline agent is for example chosen from alkanolamines, oxyethylenated and/or oxypropylenated ethylene diamines, amino acids and the compounds of formula (VI) below:

$$\begin{array}{c} Rx \\ \phantom{Rx}\diagdown \\ \phantom{Rx}\phantom{\diagdown}N-W-N \\ \phantom{Rx}\diagup \phantom{\diagdown}\phantom{N-W-N}\diagdown \\ Ry \phantom{\diagup} \phantom{N-W-N} Rt \end{array} \quad (VI)$$

wherein W is chosen from $C_1$-$C_6$ alkylene residues optionally substituted with at least one group chosen from hydroxyl and $C_1$-$C_6$ alkyl radicals; and Rx, Ry, Rz and Rt, are each independently chosen from a hydrogen atom, $C_1$-$C_6$ alkyl, $C_1$-$C_6$ hydroxyalkyl and $C_1$-$C_6$ aminoalkyl radicals.

Non-limiting examples of such amines include 1,3-diaminopropane, 1,3-diamino-2-propanol, spermine and spermidine.

As used herein, "alkanolamine" is understood to mean an organic amine comprising a primary, secondary or tertiary amine functional group and at least one linear or branched $C_1$-$C_8$ alkyl group bearing at least one hydroxyl radical.

Alkanolamines such as mono-, di- or trialkanolamines comprising one to three $C_1$-$C_4$ hydroxyalkyl radicals, which may be identical or different, may be used in the compositions disclosed herein.

Among compounds of this type, non-limiting mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and trishydroxymethylaminomethane.

Suitable amino acids that can be used in the compositions disclosed herein include, but are not limited to amino acids of natural and synthetic origin, in their L, D or racemic form, and comprise at least one acid functional group, for example carboxylic, sulphonic, phosphonic and phosphoric acid functional groups. The amino acids may be in neutral or ionic form.

Non-limiting examples of amino acids include aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to at least one embodiment, the amino acids are basic amino acids comprising an additional amine function optionally included in a ring or in a ureido function.

Exemplary basic amino acids are for instance chosen from those of formula (VII) below:

$$R-CH_2-CH\begin{array}{c}NH_2\\ \phantom{X}\\ CO_2H\end{array} \quad (VII)$$

wherein R is a group chosen from:

$$\begin{array}{c}\diagup\!\!\!\diagdown\!\!\!N\\ NH\end{array}\!\!\!\!\diagup \quad -(CH_2)_3NH_2 \quad -(CH_2)_2NH_2$$

$$-(CH_2)_2NHCONH_2 \quad -(CH_2)_2NH-\underset{\underset{NH}{\|}}{C}-NH_2$$

The compounds corresponding to formula (VII) are histidine, lysine, arginine, ornithine and citrulline.

The at least one organic amine can also be chosen from organic amines of heterocyclic type. In addition to the histidine already mentioned in the amino acids, non-limiting mention may be made of pyridine, piperidine, imidazole, triazole, tetrazole and benzimidazole.

The at least one organic amine can also be chosen from amino acid dipeptides, for example, carnosine, anserine and baleine.

According to at least one embodiment, the at least one organic amine is chosen from compounds comprising a guanidine function. In addition to the arginine already mentioned as an exemplary amino acid, other non-limiting examples include, but are not limited to creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino (imino)methyl]amino)ethane-1-sulphonic acid.

Suitable hybrid compounds include, but are not limited to guanidine carbonate and monoethanolamine hydrochloride.

In at least one embodiment, the compositions of the present disclosure comprise at least one alkanolamine and/or at least one basic amino acid, for instance, at least one alkanolamine, such as monoethanolamine.

According to the present disclosure, the at least one alkaline agent, if present in the compositions disclosed herein, is present in an amount ranging from 0.01% to 30% by weight, such as from 0.1% to 20% by weight, relative to the weight of said composition.

The compositions according to the present disclosure also comprise hydrogen peroxide.

Hydrogen peroxide is present in an amount ranging from 0.1% to 20% by weight, such as from 0.5% to 10% by weight, relative to the weight of the composition.

The compositions according to the present disclosure can further comprise oxidation dyes, direct dyes and mixtures thereof.

The oxidation dyes are chosen for example from oxidation bases and couplers.

By way of non-limiting example, the oxidation bases are chosen from para-phenylenediamines, bisphenylalkylenediamines, para-aminophenols, ortho-aminophenols, heterocyclic bases and their addition salts.

Non-limiting mention may be made of para-phenylenediamines, such as para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine and the acid addition salts thereof.

In at least one embodiment, para-phenylenediamine, para-tolylenediamine, 2-isopropyl-para-phenylenediamine, 2-(β-hydroxyethyl)-para-phenylenediamine, 20-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and the acid addition salts thereof may be used.

Non-limiting mention of bisphenylalkylenediamines include, but are not limited to N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Suitable para-aminophenols include but are not limited to para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl) phenol, 4-amino-2-(aminometh-yl)phenol, 4-amino-2-[(β-hydroxyethyl)aminomethyl]phenol, 4-amino-2-fluorophenol and the acid addition salts thereof.

Exemplary ortho-aminophenols, include, by way of example, 2-aminophenol, 2-amino-5-methylphenol, 2-amino-6-methylphenol, 5-acetamido-2-aminophenol and their addition salts.

Non-limiting mention may be made, among heterocyclic bases, of pyridine derivatives, pyrimidine derivatives and pyrazole derivatives.

Suitable examples of pyridine derivatives, include the compounds disclosed, for example, in Great Britain Patent Nos. GB 1 026 978 and GB 1 153 196, such as 2,5-diaminopyridine, 2-[(4-methoxyphenyl)amino]-3-aminopyridine, 3,4-diaminopyridine and the addition salts thereof.

Examples of pyridine oxidation bases that may be used according to the present disclosure include, but are not limited to 3-aminopyrazolo[1,5-a]pyridine oxidation bases and the addition salts thereof disclosed, for example, in French Patent Application No. 2 801 308. Mention may be made, by way of non-limiting example, of pyrazolo[1,5-a]pyridin-3-ylamine; 2-(acetylamino)pyrazolo[1,5-a]pyridin-3-ylamine; 2-(morpholin-4-yl)-pyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl) ethanol; (3-aminopyrazolo[1,5-a]pyridin-2-yl)methanol; 3,6-diaminopyrazolo[1,5-a]pyridine; 3,4-diaminopyrazolo [1,5-a]pyridine; pyrazolo[1,5-a]pyridine-3,7-diamine; 7-(morpholin-4-yl)pyrazolo[1,5-a]pyridin-3-ylamine; pyrazolo[1,5-a]pyridine-3,5-diamine; 5-(morpholin-4-yl)pyrazolo[1,5-a]pyridin-3-ylamine; 2-[(3-aminopyrazolo[1,5-a] pyridin-5-yl)(2-hydroxyethyl)amino]ethanol; 2-[(3-aminopyrazolo[1,5-a]pyridin-7-yl)(2-hydroxyethyl)amino] ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and the addition salts thereof.

Mention may be made, among pyrimidine derivatives, of the compounds described, for example, in German Patent No. 2 359 399; Japanese Patent Nos. 2526099 and 05-63124; European Patent No. 0 770 375 and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Non-limiting mention may be made, among pyrazole derivatives, of the compounds described in German Patent Nos. 3 843 892, 4 133 957, and 195 43 988, and International Patent Application Nos. WO 94/08969, and WO 94/08970, and French Patent Application No. 2 733 749, such as 4,5-diamino-1-methylpyrazole, 4,5-diamino-1-(β-hydroxyethyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl- 1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and the addition salts thereof. In at least one embodiment, 4,5-diamino-1-(β-methoxyethyl)pyrazole may be used.

According to at least one embodiment, use will be made of a 4,5-diaminopyrazole, such as 4,5-diamino-1-(β-hydroxyethyl)pyrazole and/or one of its salts.

Non-limiting mention may also be made of pyrazole derivatives such as diamino-N,N-dihydropyrazolopyrazolones, for example those disclosed in French Patent Application 2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-[3-(dimethylamino)pyrrolidin-1-yl]-1,2-diethyl-1,2-dihydropyrazol-3-one and 2,3-diamino-6-hydroxy-6,7-dihydro-1H,5H-pyrazolo[1,2-a]pyrazol-1-one.

In at least one embodiment, 2,3-diamino-6,7-dihydro-1H,5H-pyrazolo[1,2-a]pyrazol-1-one and/or one of its salts may be used.

Suitable heterocyclic bases include, but are not limited to 4,5-diamino-1-(β-hydroxyethyl)pyrazole and/or 2,3-diamino-6,7-dihydro-1H,5H-pyrazolo[1,2-a]pyrazol-1-one and/or addition salts thereof.

The compositions according to the present disclosure can optionally comprise at least one coupler conventionally used for dyeing keratin fibers.

Mention may be made, among these couplers, of meta-phenylenediamines, meta-aminophenols, meta-diphenols, naphthalene couplers or heterocyclic couplers and their addition salts.

Other suitable examples include, but are not limited to 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole, 6-methylpyrazolo[1,5-a]benzimidazole, the acid addition salts and mixtures thereof.

The addition salts of the oxidation bases and couplers are for example chosen from acid addition salts such as hydrochlorides, hydrobromides, sulphates, citrates, succinates, tartrates, lactates, tosylates, benzenesulphonates, phosphates and acetates.

The at least one oxidation base is present in an amount ranging from 0.0001% to 10% by weight, relative to the total weight of the emulsion, such as from 0.005% to 5% by weight, relative to the total weight of the composition.

The at least one coupler, if present, is present in an amount ranging from 0.0001% to 10% by weight, relative to the total weight of the emulsion, such as from 0.005% to 5% by weight relative to the total weight of the composition.

The direct dyes that can be used in the compositions of the present disclosure are, for example, synthetic and natural dyes, chosen from ionic and nonionic, for example cationic and nonionic direct dyes.

Suitable examples of direct dyes include, but are not limited to nitrobenzene dyes; azo, azomethine and methine direct dyes; azocarbocyanines, such as tetraazacarbocyanines (tetraazapentamethines); quinone, such as anthraquinone, naphthoquinone and benzoquinone; azine; xanthenes; triarylmethane; indoamine; indigoid; phthalocyanine; and porphyrin direct dyes and natural direct dyes, and mixtures thereof. According to at least one embodiment, non-limiting mention may be made of azo, methine, carbonyl, azine, nitro (hetero)aryl or tri(hetero)arylmethane direct dyes, porphyrins, phthalocyanines and natural direct dyes, and mixtures thereof.

Among the benzene direct dyes that can be used according to the present disclosure, mention may be made, in a nonlimiting manner, of the following compounds:

1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris-(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Among the azo, azomethine, methine, and tetraazapentamethine direct dyes that can be used according to the present disclosure, non-limiting mention may be made of the cationic dyes disclosed in International Patent Application Nos. WO 95/15144 and WO 95/01772 and European Patent Application Nos. 0 714 954, 1 378 544, and 1 674 073; and French Application Nos. 2189006, 2285851, and 2140205.

In at least one embodiment of the present disclosure, the dyes of formulae (I) to (IV) may be used, such as the compounds of formulae (II), (III), (IV) and (IV'):

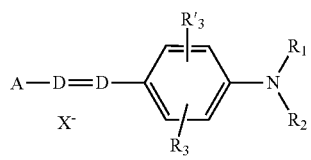
(II)

wherein:

each instance of D is chosen from a nitrogen atom and a —CH group, such as a nitrogen atom, $R_1$ and $R_2$, are each independently chosen from a hydrogen atom; $C_1$-$C_4$ alkyl radicals which can be substituted with a —CN, —OH or —NH$_2$ radical, or may form, with a carbon atom of the benzene ring, a heterocycle which is optionally oxygenated or nitrous and which can be substituted with at least one $C_1$-$C_4$ alkyl radical; such as a 4'-aminophenyl radical, $R_3$ and $R'_3$, are each independently chosen from a hydrogen atom, halogen atoms chosen from chlorine, bromine, iodine and fluorine, cyano, $C_1$-$C_4$ alkyl, $C_1$-$C_4$ alkoxy and acetyloxy radicals, X$^-$ is an anion for example, chosen from chloride, methyl sulphate and acetate, A is a group chosen from the structures A1 to A18, and in at least one embodiment chosen from A1, A4, A7, A13 and A18:

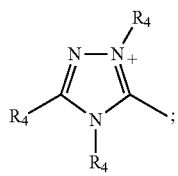
A1

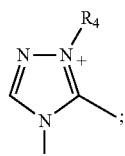
A2

A3

A4

-continued

A5

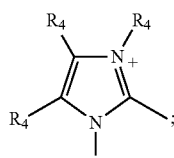
A6

A7

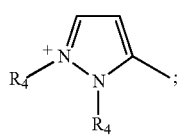
A8

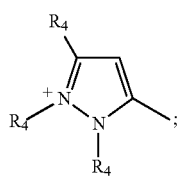
A9

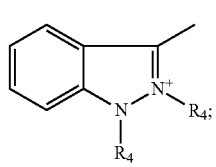
A10

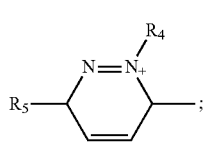
A11

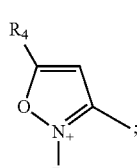
A12

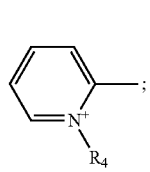
A13

-continued

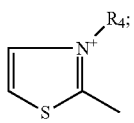
A14

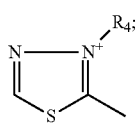
A15

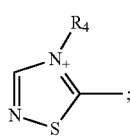
A16

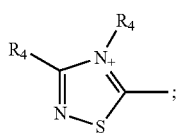
A17

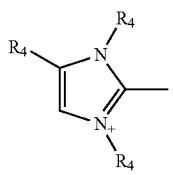
A18 wherein $R_4$ is chosen from $C_1$-$C_4$ alkyl radicals which can be substituted with a hydroxyl radical and $R_5$ is chosen from $C_1$-$C_4$ alkoxy radicals;

$X^-$ is an anion, such as chloride, methyl sulphate and acetate,

B is a group chosen from the structures B1 to B6 below:

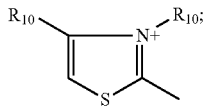
B1

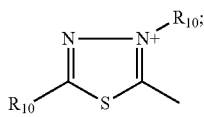
B2

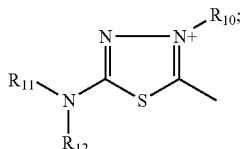
B3

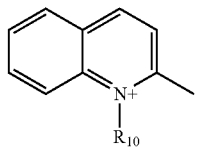
B4

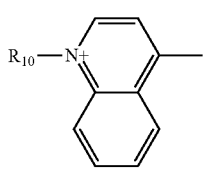
B5

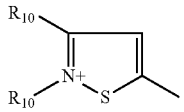
B6 wherein $R_{10}$ is chosen from $C_1$-$C_4$ alkyl radicals, and $R_{11}$ and $R_{12}$, are each independently chosen from a hydrogen atom and $C_1$-$C_4$ alkyl radicals;

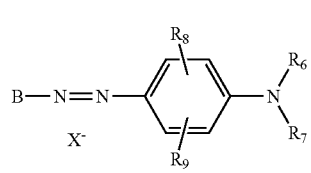
(III)

wherein:

$R_6$ is chosen from a hydrogen atom and $C_1$-$C_4$ alkyl radicals, $R_7$ is chosen from a hydrogen atom, alkyl radicals which can be substituted with a —CN radical or with an amino group, 4'-aminophenyl radicals, or forms, with $R_6$, a heterocycle which is optionally oxygenated and/or nitrous and which can be substituted with a $C_1$-$C_4$ alkyl radical, $R_8$ and $R_9$, are each independently chosen from a hydrogen atom, halogen such as bromine, chlorine, iodine an fluorine, $C_1$-$C_4$ alkyl radicals, $C_1$-$C_4$ alkoxy radicals, and a —CN radical,

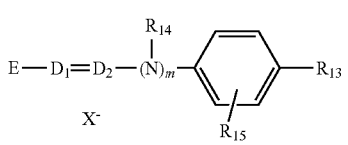
(IV)

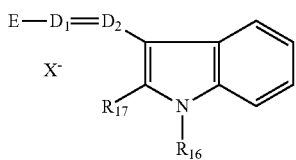
(IV')

wherein:

$R_{13}$ is chosen from a hydrogen atom, $C_1$-$C_4$ alkoxy radicals and halogens such as bromine, chlorine, iodine and fluorine, $R_{14}$ is chosen from a hydrogen atom, $C_1$-$C_4$ alkyl radicals, or forms, with a carbon atom of the benzene ring, a heterocycle which is optionally oxygenated and/or substituted with at least one $C_1$-$C_4$ alkyl group, $R_{15}$ is chosen from a hydrogen atom and halogens such as bromine, chlorine, iodine and fluorine, $R_{16}$ and $R_{17}$, are each independently chosen from a hydrogen atom and $C_1$-$C_4$ alkyl radicals, $D_1$ and $D_2$ are each independently chosen from a nitrogen atom and a —CH group, m=0 or 1, it being understood that, when $R_{13}$ is an unsubstituted amino group, then $D_1$ and $D_2$ are —CH groups and m=0, $X^-$ is an anion chosen from chloride, methyl sulphate and acetate, E is a group chosen from the structures E1 to E8, such as E1, E2 and E7, below:

E1

R'—N+ ⟨pyridinium⟩ ;

E2

⟨2-pyridinium with R'⟩ ;

E3

⟨pyrimidinone with R', R'⟩ ;

E4

⟨pyrimidinone with R', R', R'⟩ ;

E5

⟨hydroxy-methyl-indazolium with R', R'⟩ ;

E6

⟨benzothiazolium with R'⟩ ;

E7

⟨3-methylpyridinium with R'⟩ et

E8

⟨triazolium with R', R'⟩ ;

wherein R' is chosen from $C_1$-$C_4$ alkyl radicals;

and when m=0 and $D_1$ is a nitrogen atom, then E can also be a group of structure E9 below:

E9

⟨imidazolium with R', R'⟩ ;

wherein R' is chosen from $C_1$-$C_4$ alkyl radicals;

$$G\!-\!N\!=\!N\!-\!J \qquad (V)$$

wherein:

G is a group chosen from the structures $G_1$ to $G_3$ below:

$G_1$

⟨pyrazolium with $R_{19}$, $R_{18}$, $R_{20}$, $R_{21}$, $X^-$⟩

$G_2$

⟨five-membered ring with $R_{20}$, $R_{21}$, $R_{18}$, Z, $X^-$⟩

$G_3$

⟨six-membered ring with $R_{23}$, $R_{24}$, K, P, M⟩ wherein for structures $G_1$ to $G_3$, $R_{18}$ is chosen from $C_1$-$C_4$ alkyl radicals, and a phenyl radical which can be substituted with a $C_1$-$C_4$ alkyl radical or a halogen atom chosen from chlorine, bromine, iodine and fluorine, $R_{19}$ is chosen from $C_1$-$C_4$ alkyl radicals and a phenyl radical, $R_{20}$ and $R_{21}$, are each independently chosen from $C_1$-$C_4$ alkyl radicals and a phenyl radical, or together form in $G_1$ a benzene ring substituted with at least one radical chosen from $C_1$-$C_4$ alkyl, $C_1$-$C_4$ alkoxy and $NO_2$ radicals, or together form in $G_2$ a benzene ring optionally substituted with at least one radical chosen from $C_1$-$C_4$ alkyl, $C_1$-$C_4$ alkoxy and $NO_2$ radicals, $R_{20}$ can also be a hydrogen atom, Z is chosen from oxygen, sulphur and —$NR_{19}$, M is chosen from —CH, —CR, wherein R is chosen from $C_1$-$C_4$ alkyl radicals, and —$NR_{22}(X^-)_r$, K is chosen from —CH, —CR, wherein R is chosen from $C_1$-$C_4$ alkyl radicals, and —$NR_{22}(X^-)_r$, P is chosen from —CH, —CR, wherein R is chosen from $C_1$-$C_4$ alkyl radicals, —$NR_{22}(X^-)_r$; wherein r is zero or 1, $R_{22}$ is chosen from oxygen, $C_1$-$C_4$ alkoxy radicals, and $C_1$-$C_4$ alkyl radicals, $R_{23}$ and $R_{24}$, are independently chosen from a hydrogen atom, halogens chosen from chlorine, bromine, iodine and fluorine, $C_1$-$C_4$ alkyl radicals, $C_1$-$C_4$ alkoxy radicals, and —$NO_2$ radical, $X^-$ is an anion chosen from chloride, iodide, methyl sulphate, ethyl sulphate, acetate and perchlorate, with the proviso that, if $R_{22}$ is $O^-$, then r is zero, if K or P or M is —N—$(C_1$-$C_4)$alkyl $X^-$, then $R_{23}$ or $R_{24}$ is or is not different from a hydrogen atom, if K is —$NR_{22}(X^-)_r$, then M=P=—CH or —CR, if M is —$NR_{22}(X^-)_r$, then K=P=—CH or —CR, if P is —$NR_{22}(X^-)_r$, then K=M and is chosen from —CH and —CR, if Z is a sulphur atom and $R_{21}$ is a $C_1$-$C_4$ alkyl radical, then $R_{20}$ is not a hydrogen atom, if Z is —$NR_{22}$ and $R_{19}$ is a $C_1$-$C_4$ alkyl radical, then at least one of the radicals $R_{18}$, $R_{20}$ or $R_{21}$ of the group of structure $G_2$ is different from a $C_1$-$C_4$ alkyl radical, J is chosen from:

(a) a group of structure $J_1$ below:

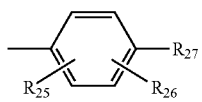

wherein:

$R_{25}$ is chosen from a hydrogen atom, halogens chosen from chlorine, bromine, iodine and fluorine, $C_1$-$C_4$ alkyl radicals, $C_1$-$C_4$ alkoxy radicals, —OH, —$NO_2$, —$NHR_{28}$, —$NR_{29}R_{30}$ and —$NHCO(C_1$-$C_4)$alkyl radicals, or forms, with $R_{26}$, a 5- or 6-membered ring possibly comprising at least one heteroatom chosen from nitrogen, oxygen and sulphur, $R_{26}$ is chosen from a hydrogen atom, halogens chosen from chlorine, bromine, iodine and fluorine, $C_1$-$C_4$ alkyl radicals and $C_1$-$C_4$ alkoxy radicals, or forms, with $R_{27}$ or $R_{28}$, a 5- or 6-membered ring possibly comprising at least one heteroatom chosen from nitrogen, oxygen and sulphur, $R_{27}$ is chosen from a hydrogen atom, —OH, —$NHR_{28}$ radicals and —$NR_{29}R_{30}$ radicals, $R_{28}$ is chosen from a hydrogen atom, $C_1$-$C_4$ alkyl radicals, $C_1$-$C_4$ monohydroxyalkyl radicals, $C_2$-$C_4$ polyhydroxyalkyl radicals and phenyl radicals, $R_{29}$ and $R_{30}$, are each independently chosen from $C_1$-$C_4$ alkyl radicals, $C_1$-$C_4$ monohydroxyalkyl radicals and $C_2$-$C_4$ polyhydroxyalkyl radicals;

(b) a 5- or 6-membered nitrous heterocyclic group capable of comprising other heteroatoms and/or carbonyl groups and which can be substituted with at least one radical chosen from $C_1$-$C_4$ alkyl, amino and phenyl radicals, a group of structure $J_2$ below:

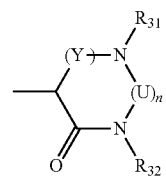

wherein:

$R_{31}$ and $R_{32}$, are each independently chosen from a hydrogen atom, $C_1$-$C_4$ alkyl radicals and phenyl radicals, Y is chosen from —CO— and

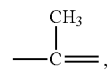

n=0 or 1, wherein, when n is 1, U is —CO—.

In the structures (II) to (V) defined above, the $C_1$-$C_4$ alkyl or alkoxy groups are chosen from, in at least one embodiment, methyl, ethyl, butyl, methoxy and ethoxy.

Non-limiting examples of the compounds of formulae (II) and (IV), include, but are not limited to:

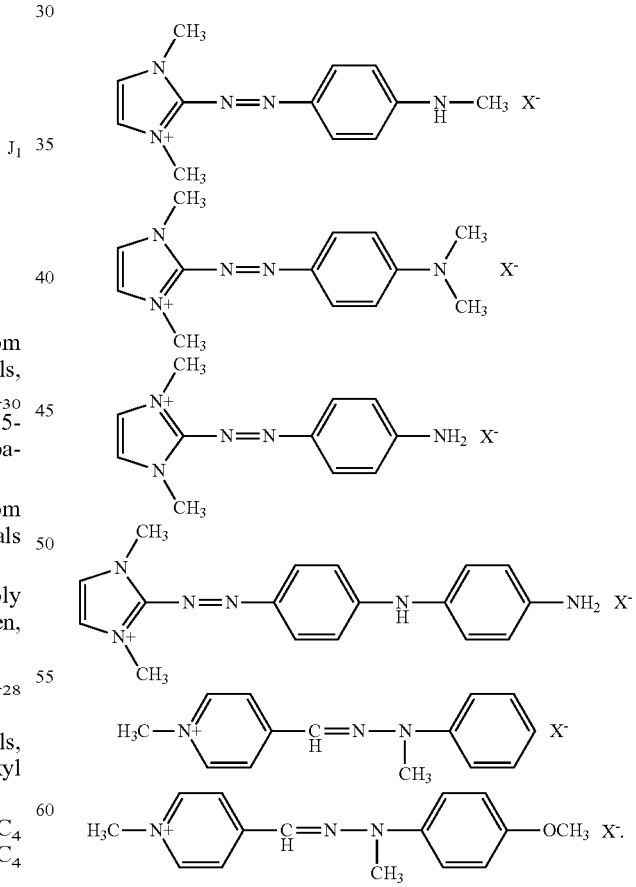

Among the azo direct dyes, non-limiting mention may also be made of the following dyes described in the Colour Index International, 3rd Edition:

Disperse Red 17,
Basic Red 22,
Basic Red 76,
Basic Yellow 57,
Basic Brown 16,
Basic Brown 17, and
Disperse Black 9.

Non-limiting mention may also be made of 1-(4'-aminodiphenylazo)-2-methyl-4-bis(β-hydroxyethyl)aminobenzene.

Among the quinine direct dyes, non-limiting mention may be made of the following dyes:
Disperse Red 15,
Solvent Violet 13,
Disperse Violet 1,
Disperse Violet 4,
Disperse Blue 1,
Disperse Violet 8,
Disperse Blue 3,
Disperse Red 11,
Disperse Blue 7,
Basic Blue 22,
Disperse Violet 15,
Basic Blue 99,
and also the following compounds:
1-N-methylmorpholiniumpropylamino-4-hydroxyanthraquinone,
1-Aminopropylamino-4-methylaminoanthraquinone,
1-Aminopropylaminoanthraquinone,
5-β-hydroxyethyl-1,4-diaminoanthraquinone,
2-Aminoethylaminoanthraquinone, and
1,4-bis(β,γ-dihydroxypropylamino)anthraquinone.

Among the azine dyes, non-limiting mention may be made of the following compounds:
Basic Blue 17, and
Basic Red 2.

Among the triarylmethane dyes that can be used according to the present disclosure, non-limiting mention may be made of the following compounds:
Basic Green 1,
Basic Violet 3,
Basic Violet 14,
Basic Blue 7, and
Basic Blue 26.

Among the indoamine dyes that can be used according to the present disclosure, non-limiting mention may be made of the following compounds:
2-β-hydroxyethlyamino-5-[bis(β-4'-hydroxyethyl)amino]anilino-1,4-benzoquinone,
2-β-hydroxyethylamino-5-(2'-methoxy-4'-amino)anilino-1,4-benzoquinone,
3-N (2'-Chloro-4'-hydroxy)phenyl-acetylamino-6-methoxy-1,4-benzoquinoneimine,
3-N(3'-Chloro-4'-methylamino)phenylureido-6-methyl-1,4-benzoquinoneimine, and
3-[4'-N-(Ethyl,carbamylmethyl)amino]phenylureido-6-methyl-1,4-benzoquinoneimine.

Among the tetraazapentamethine-type dyes that can be used according to the present disclosure, non-limiting mention may be made of the following compounds:

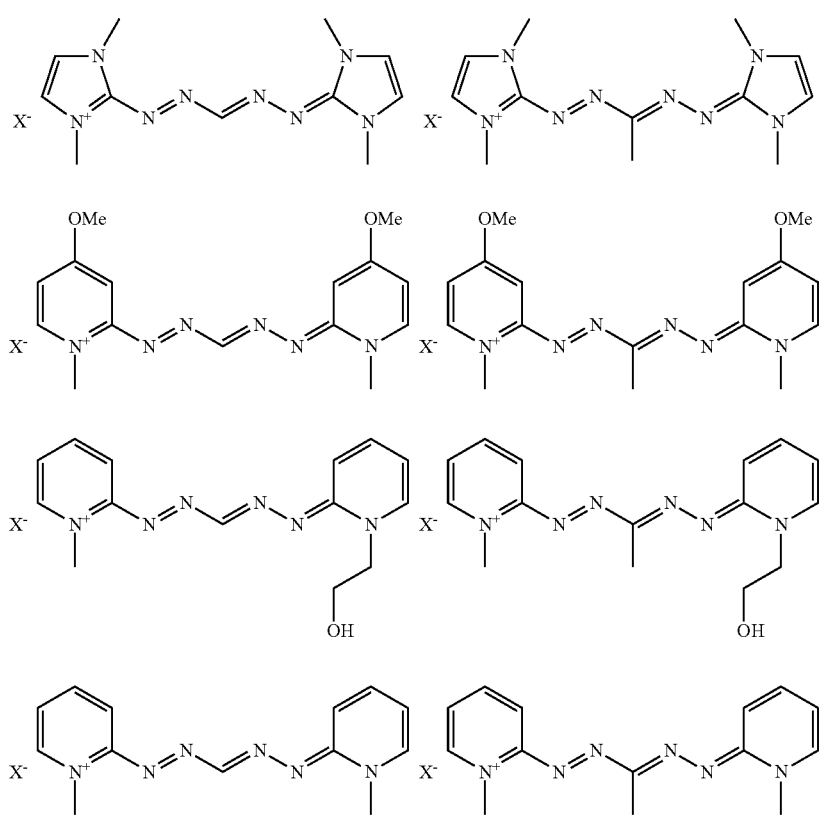

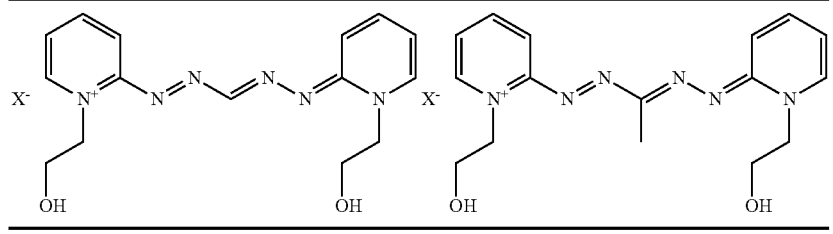

$X^-$ is an anion chosen from chloride, iodide, methyl sulphate, ethyl sulphate, acetate and perchlorate.

Among the natural direct dyes that can be used according to the disclosure, non-limiting mention may be made of lawsone, juglone, alizarin, purpurin, carminic acid, kermesic acid, purpurogallin, protocatechaldehyde, indigo, isatin, curcumin, spinulosin, apigenidin, hematoxylin, hematein, brasilin, brasilein and orceins. It is also possible to use extracts or decoctions comprising these natural dyes, such as henna-based poultices and extracts.

Exemplary direct dyes that may be used include, but are not limited to monochromophoric dyes (i.e. comprising just one dye) and polychromophoric dyes, such as di- and trichromophoric dyes; it being possible for the chromophores to be identical or different and from the same chemical family or different chemical families. It should be noted that a polychromophoric dye comprises several radicals each derived from a molecule which absorbs in the visible range between 400 and 800 nm. Furthermore, this absorbance by the dye requires neither prior oxidation thereof nor combination with at least one other chemical species.

The chromophores in the polychromophoric dyes are connected together by at least one linker arm which may be cationic or noncationic.

In at least one embodiment, the linker arm is chosen from linear, branched and cyclic $C_1$-$C_{20}$ alkyl chains, optionally interrupted with at least one heteroatom, such as nitrogen or oxygen, and/or with at least one group comprising a heteroatom, such as CO and $SO_2$, optionally interrupted with at least one heterocycle that may or may not be fused to a phenyl nucleus and comprising at least one quaternized nitrogen atom in the ring and optionally at least one other heteroatom, such as oxygen, nitrogen and sulphur, optionally interrupted with at least one substituted or unsubstituted phenyl or naphthyl group, optionally interrupted with at least one quaternary ammonium group substituted with two optionally substituted $C_1$-$C_{15}$ alkyl groups; wherein the linker arm does not comprise a nitro, nitroso or peroxo group.

If the heterocycles or aromatic nuclei (phenyl or naphthyl) are substituted, they are substituted, for example, with at least one radical chosen from $C_1$-$C_8$ alkyl radicals optionally substituted with group chosen from hydroxyl, $C_1$-$C_2$ alkoxy, $C_2$-$C_4$ hydroxyalkoxy, acetylamino and amino groups substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different from nitrogen; halogens; hydroxyl; $C_1$-$C_2$ alkoxy radicals; $C_2$-$C_4$ hydroxyalkoxy radicals; amino radicals; amino radicals substituted with one or two identical or different $C_1$-$C_4$ alkyl radicals, optionally bearing at least one hydroxyl group.

Among the polychromophoric dyes, non-limiting mention may be made of symmetrical and nonsymmetrical azo and/or azomethine (hydrazone) di- or trichromophoric dyes comprising, in one alternative, at least one optionally fused 5- or 6-membered aromatic heterocycle, comprising at least one quaternized nitrogen atom in the heterocycle and optionally at least one other heteroatom, such as nitrogen, sulphur or oxygen, and, as another alternative, at least one optionally substituted phenyl or naphthyl group, optionally bearing at least one group OR wherein R is chosen from a hydrogen atom, optionally substituted $C_1$-$C_6$ alkyl radicals, an optionally substituted phenyl nucleus, and at least one group $N(R')_2$ wherein each instance of R', is independently chosen from a hydrogen atom, optionally substituted $C_1$-$C_6$ alkyl radicals and an optionally substituted phenyl nucleus; it being possible for the radicals R' to form, with the nitrogen atom to which they are attached, a saturated 5- or 6-membered heterocycle, or alternatively one and/or both radicals R' may each form, with the carbon atom of the aromatic ring located ortho to the nitrogen atom, a saturated 5- or 6-membered heterocycle.

Exemplary aromatic cationic heterocycles that may be mentioned include, but are not limited to 5- or 6-membered rings comprising 1 to 3 nitrogen atoms, such as 1 or 2 nitrogen atoms, wherein one is quaternized; and wherein the heterocycle is optionally fused to a benzene nucleus. In at least one embodiment, the heterocycles may optionally comprise another heteroatom other than nitrogen, such as sulphur or oxygen.

The bonding between the linker arm, as defined above, and each chromophore is, for example, via a heteroatom substituent on the phenyl or naphthyl nucleus or via the quaternized nitrogen atom of the cationic heterocycle.

The dyes in accordance with the present disclosure may comprise identical or different chromophores.

Non-limiting examples include those disclosed in European Patent Nos. 1 637 566, 1 619 221, 1 634 926, 1 619 220, 1 672 033, 1 671 954, 1 671 955, 1 679 312, 1 671 951, 0 167 952, 0 167 971, 1 408 919, 1 377 264, 1 377 262, 1 377 261, 1 377 263, 1 399 425, 1 399 117, 1 416 909, 1 399 116 and 1 671 560, and International Patent Application Nos. WO 06/063866, WO 06/063867, WO 06/063868, and WO 06/063869.

Other suitable examples of cationic direct dyes are mentioned in European Patent Application No. 1 006 153, which discloses dyes comprising two chromophores of anthraquinone type connected by means of a cationic linker arm; European Patent Application Nos. 1 433 472, 1 433 474, 1 433 471 and 1 433 473, which discloses identical or different dichromophoric dyes connected via a cationic or noncationic linker arm, and also European Patent Application No. 6 291 333 which discloses dyes comprising three chromophores, one of them being an anthraquinone chromophore to which are attached the two chromophores of azo or diazacarbocyanine type or an isomer thereof.

When they are present, the at least one direct dye is present in an amount ranging from 0.0001% to 10% by weight of the total weight of the composition, such as from 0.005% to 5% by weight.

The compositions according to the present disclosure may further comprise at least one surfactant.

According to at least one embodiment, the at least one surfactant is chosen from nonionic surfactants and anionic surfactants.

The anionic surfactants are for example chosen from salts, such as alkali metal salts, for instance sodium salts, ammonium salts, amine salts, amino alcohol salts and alkaline earth metal salts such as magnesium salts. Non-limiting examples of the at least one anionic surfactant include, but are not limited to:

alkyl sulphates, alkyl ether sulphates, alkylamido ether sulphates, alkylaryl polyether sulphates, and monoglyceride sulphates;

alkylsulphonates, alkylamidesulphonates, alkylarylsulphonates, α-olefin sulphonates, and paraffin sulphonates;

alkyl phosphates and alkyl ether phosphates;

alkylsulphosuccinates, alkyl ether sulphosuccinates, alkylamide sulphosuccinates, and alkyl sulphosuccinamates;

alkyl sulphoacetates;

acylsarcosinates, acylisethionates and N-acyltaurates;

salts of fatty acids such as oleic acid, ricinoleic acid, palmitic acid and stearic acid, coconut oil acid and hydrogenated coconut oil acid;

alkyl-D-galactosiduronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, such as those comprising from 2 to 50 ethylene oxide groups;

and mixtures thereof;

wherein the alkyl or acyl radical of these various compounds comprise from 6 to 24 carbon atoms, such as from 8 to 24 carbon atoms, and the aryl radical is chosen from a phenyl and benzyl groups.

The nonionic surfactants are for instance chosen from monooxyalkylenated and polyoxyalkylenated, monoglycerolated and polyglycerolated nonionic surfactants. The oxyalkylene units are for example oxyethylene or oxypropylene units, or a combination thereof, such as oxyethylene units.

Non-limiting example of oxyalkylenated nonionic surfactants include, but are not limited to:

oxyalkylenated ($C_8$-$C_{24}$)alkylphenols, saturated and unsaturated, linear and branched, oxyalkylenated $C_8$-$C_{30}$ alcohols, saturated and unsaturated, linear and branched, oxyalkylenated $C_8$-$C_{30}$ amides, esters of saturated and unsaturated, linear and branched $C_8$-$C_{30}$ acids and of polyethylene glycols, polyoxyethylenated esters of saturated and unsaturated, linear and branched $C_8$-$C_{30}$ acids and of sorbitol, saturated and unsaturated, oxyethylenated plant oils, and condensates of ethylene oxide and/or of propylene oxide, and mixtures thereof.

The at least one surfactant comprises a number of moles of ethylene oxide and/or of propylene oxide ranging from 1 to 100, such as from 2 to 50, for example from 2 to 30. In at least one embodiment, the at least one nonionic surfactant does not comprise any oxypropylene units.

In accordance with at least one embodiment of the present disclosure, the oxyalkylenated nonionic surfactants are chosen from oxyethylenated $C_8$-$C_{30}$ alcohols comprising from 1 to 100 mol of ethylene oxide, and polyoxyethylenated esters of saturated and unsaturated, linear and branched $C_8$-$C_{30}$ acids and of sorbitol comprising from 1 to 100 mol of ethylene oxide.

By way of example of monoglycerolated or polyglycerolated nonionic surfactants, monoglycerolated and polyglycerolated $C_8$-$C_{40}$ alcohols are used in at least one embodiment.

Non-limiting mention may be made of monoglycerolated and polyglycerolated $C_8$-$C_{40}$ alcohols corresponding to the following formula:

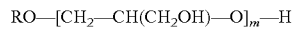

wherein R is chosen from linear and branched $C_8$-$C_{40}$ alkyl and alkenyl radicals, such as $C_8$-$C_{30}$, alkyl and alkenyl radicals, and m is a number ranging from 1 to 30, such as from 1 to 10.

Non-limiting examples of surfactants include, but are not limited to lauryl alcohol comprising 4 mol of glycerol (INCI name: Polyglyceryl-4-Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol may in at least one embodiment, be present as a mixture of alcohols, for example in a commercial product, several species of polyglycerolated fatty alcohols may coexist in the form of a mixture.

Suitable monoglycerolated and polyglycerolated alcohols include, but are not limited to $C_8$-$C_{10}$ alcohols comprising 1 mol of glycerol, $C_{10}$-$C_{12}$ alcohols comprising 1 mol of glycerol and $C_{12}$ alcohols comprising 1.5 mol of glycerol.

In at least one embodiment, the at least one surfactant optionally present in the composition is a nonionic surfactant.

The at least one surfactant is present in the compositions disclosed herein in an amount ranging from 0.1% to 50% by weight, such as from 0.5% to 30% by weight, relative to the weight of the composition.

The compositions disclosed herein may further comprise at least one adjuvant conventionally used in compositions for dyeing or lightening the hair, such as anionic, cationic and nonionic polymers, and blends thereof; antioxidants; penetration agents; sequestering agents; fragrances; dispersants; film-forming agents; ceramides; preservatives; and opacifiers.

The at least one adjuvant can be present in an amount, independently, ranging from 0.01% to 20% by weight, relative to the weight of the composition.

The compositions according to the present disclosure may further comprise at least one fumed silica.

The at least one fumed silica may be obtained by high-temperature hydrolysis of a volatile silicon compound in an oxhydric flame, producing a finely divided silica. This process makes it possible for instance to obtain hydrophilic silicas which have a large number of silanol groups at their surface. Such hydrophilic silicas are, for example, sold under the names AEROSIL 130®, AEROSIL 200®, AEROSIL 255®, AEROSIL 300®, and AEROSIL 380® by the company Degussa, and CAB-O-SIL HS-5®, CAB-O-Sil EH-5®, CAB-O-SIL LM-130®, CAB-O-SIL MS-55® and CAB-O-SIL M-5® by the company Cabot.

It at least one embodiment, the surface of the silica is modified chemically to reduce the number of silanol groups. Silanol groups may for instance be substituted with hydrophobic groups resulting in a hydrophobic silica.

The hydrophobic groups may be chosen from:

trimethylsiloxyl groups, which are obtained for instance by treating fumed silica in the presence of hexamethyldisilazane. Silicas thus treated are known as "Silica silylate" according to the CTFA (6th Edition, 1995). They are, for example, sold under the references AEROSIL R812® by the company Degussa and CAB-O-SIL TS-530® by the company Cabot; and dimethylsilyloxyl and polydimethylsiloxane groups, which are for example obtained by treating fumed silica in the presence of polydimethylsiloxane or dimethyldichlorosilane. Silicas thus treated are known as "Silica dimethyl silylate" according to the CTFA (6th Edition, 1995). They are, for example, sold under the references AEROSIL R972® and AEROSIL R974® by the company Degussa and CAB-O-SIL TS-610® and CAB-O-SIL TS-720® by the company Cabot.

The fumed silica has, for example, a particle size that may be nanometric to micrometric, for example ranging from 5 to 200 nm.

When present, the fumed silica is present in an amount ranging from 1% to 30% by weight relative to the weight of the composition.

The composition may further comprise at least one organic thickener.

The at least one thickener may be chosen from fatty acid amides, such as coconut diethanolamide an monoethanolamide, and oxyethylenated alkyl ether carboxylic acid monoethanolamide; polymeric thickeners such as cellulose-based thickeners, for instance, hydroxyethylcellulose, hydroxypropylcellulose, and carboxymethylcellulose; guar gum and derivatives thereof, such as hydroxypropylguar; gums of microbial origin, such as xanthan gum and scleroglucan gum; crosslinked homopolymers of acrylic acid and of acrylamidopropanesulphonic acid; and associative polymers, such as polymers comprising hydrophilic regions and hydrophobic regions with a fatty chain, for example alkyl and alkenyl comprising at least 10 carbon atoms capable, in an aqueous medium, of reversibly associating with one another or with other molecules).

According to at least one embodiment, the organic thickener is chosen from cellulose-based thickeners (hydroxyethylcellulose, hydroxypropylcellulose, carboxymethylcellulose), guar gum and derivatives thereof (hydroxypropylguar), gums of microbial origin (xanthan gum, scleroglucan gum), crosslinked homopolymers of acrylic acid or of acrylamidopropanesulphonic acid, and for instance from cellulose-based thickeners, such as with hydroxyethylcellulose.

The at least one organic thickener, if present, is present in an amount ranging from 0.01% to 20% by weight, such as from 0.1% to 5% by weight, relative to the weight of the composition.

The compositions according to the present disclosure may further comprise water and/or at least one organic solvent.

Non-limiting examples of the at least one organic solvent include, but are not limited to linear and branched, such as saturated, monoalcohols and diols comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol and phenylethyl alcohol; polyols with more than two hydroxyl functions, such as glycerol; polyol ethers such as ethylene glycol monomethyl, monoethyl and monobutyl ethers, propylene glycol or ethers thereof, for instance propylene glycol monomethyl ether; and also diethylene glycol alkyl ethers, such as $C_1$-$C_4$, for instance diethylene glycol monoethyl ether or monobutyl ether, and mixtures thereof.

The at least one organic solvent, if present, is present in an amount ranging from 1% to 40% by weight, such as 5% and 30% by weight, relative to the total weight of the dye composition.

In at least one embodiment, the compositions of the present disclosure comprise water in an amount ranging from 10% to 70%, such as from 20% to 55% of the total weight of the composition.

The dye composition according to the present disclosure may be in various forms, such as in the form of liquids, creams or gels, or in any other form suitable for dyeing keratin fibers, such as human hair.

According to at least one embodiment, the compositions disclosed herein may be in the form of a cream or a gel.

The pH of the compositions according to the present disclosure ranges from 3 to 12, such as from 5 to 11, for example from 7 to 11.

The pH may be adjusted to the desired value via acidifying or basifying agents normally used in the dyeing of keratin fibers.

The basifying agents are, for example, those previously described.

Among the acidifying agents, non-limiting mention may be made of inorganic and organic acids, such as hydrochloric acid and orthophosphoric acid, carboxylic acids such as tartaric acid, citric acid and lactic acid, and sulphonic acids.

The compositions disclosed herein may be obtained by mixing at least two different compositions, or even three or optionally more than three different compositions. At least one of the compositions which leads, by mixing, to the composition of the disclosure may be anhydrous. It should be noted that the compositions according to the present disclosure are prepared at the time of use just before being applied to the human keratin fibers.

According to at least one embodiment, the compositions according to the present disclosure may be obtained by mixing a first composition comprising at least one fatty substance, at least one basifying agent and, optionally, at least one dye chosen from oxidation dye, direct dyes and mixtures thereof, with a second composition comprising at least one oxidizing agent, and wherein the first and/or the second composition comprise at least one amphoteric polymer.

According to at least one embodiment of the disclosure, the composition according to the present disclosure is obtained by mixing a first composition comprising at least one fatty substance, a second composition comprising at least one basifying agent and, optionally, at least one dye chosen from oxidation dye, direct dyes and mixtures thereof, and a third composition comprising at least one oxidizing agent, and wherein the first and/or the second and/or the third composition comprise at least one amphoteric polymer.

In at least one embodiment, the oxidizing composition is for example, an aqueous composition, for instance, it may comprise more than 5% by weight of water, such as more than 10% by weight of water, for example more than 20% by weight of water.

The oxidizing composition may also comprise at least one organic solvent chosen from those listed previously; wherein the at least one solvent, if present, is present in an amount ranging from 1% to 40% by weight, such as from 5% to 30% by weight, relative to the weight of the oxidizing composition.

The oxidizing composition may further comprise at least one acidifying agent, such as inorganic and organic acids, such as hydrochloric acid, orthophosphoric acid and sulphuric acid, carboxylic acids such as acetic acid, tartaric acid, citric acid and lactic acid, and sulphonic acids.

According to at least one embodiment, the pH of the oxidizing composition, when it is aqueous, is less than 7.

In at least one embodiment, the concentration of hydrogen peroxide varies, for example, from 0.1% to 50%, such as from 0.5% to 20%, for instance from 1% and 15% by weight, relative to the weight of the oxidizing composition.

The dyeing process according to the present disclosure comprises applying the compositions disclosed herein to wet or dry human keratin fibers. The temperature during the process ranges, for instance, from ambient temperature (from 15 to 25° C.) to 80° C., such as from ambient temperature to 60° C.

After a leave-in time ranging from one minute to one hour, such as 5 minutes to 30 minutes, the keratin fibers are optionally rinsed with water, optionally washed with a shampoo and then rinsed with water, before being dried or left to dry.

The disclosure also relates to a two-compartment device comprising, in one compartment, a first composition comprising at least one fatty substance, at least one basifying agent and, optionally, at least one dye chosen from oxidation dyes and direct dyes; in the other compartment, a second composition comprising hydrogen peroxide; and wherein the first and/or the second composition comprise at least one amphoteric polymer, and wherein the compositions of the compartments are intended to be mixed to give the compositions disclosed herein just before application to the human keratin fibers.

The disclosure further relates to a three-compartment device comprising, in one compartment, a first composition comprising at least one fatty substance; in another compartment, a second composition comprising at least one basifying agent and, optionally, at least one dye chosen from oxidation dye and direct dyes; and in the final compartment, a third composition comprising hydrogen peroxide; wherein the first and/or the second and/or the third composition comprise at least one amphoteric polymer; and wherein the compositions of the three compartments are intended to be mixed to give the compositions according to the present disclosure, just before application to the human keratin fibers.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following examples serve to illustrate embodiments of the present disclosure without, however, exhibiting a limiting nature.

EXAMPLES

The following compositions were prepared as set forth below (the amounts are expressed as g % of active material):

| Composition 1 | |
|---|---|
| Disteardimonium hectorite (BENTONE 38 VCG) | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |

| Composition 2 | |
|---|---|
| Pentasodium pentetate | 1 |
| Sodium metabisulphite | 0.7 |
| Monoethanolamine | 14.5 |
| 2,5-Toluenediamine | 2.25 |
| 2,4-Diaminophenoxyethanol hydrochloride | 0.05 |
| Resorcinol | 2 |
| m-aminophenol | 0.36 |
| Hydroxyethylcellulose (NATROSOL 250 HHR, Aqualon) | 1.5 |
| Hexylene glycol | 3 |
| Dipropylene glycol | 3 |
| Ethanol | 8.25 |
| Propylene glycol | 6.2 |
| Ascorbic acid | 0.25 |
| Water | Qs 100 |

| Compositions 3 and 3' | | |
|---|---|---|
| | Comp 3 | Comp 3' |
| Pentasodium pentetate | 0.15 | 0.15 |
| Hydrogen peroxide (aqueous 50% solution) | 12 | 12 |
| Sodium stannate | 0.04 | 0.04 |
| Phosphoric acid | Qs pH 2.2 | Qs pH 2.2 |
| Tetrasodium pyrophosphate | 0.03 | 0.03 |
| Liquid petroleum jelly | 20 | 20 |
| Acrylic acid/acrylamidopropyltrimethyl-ammonium chloride copolymer provided by the company Stockhausen under the name POLYMER W3794 | 0.3 | |
| Dimethyldiallylammonium chloride/acrylic acid copolymer provided by the company Nalco under the name MERQUAT 280 | | 0.3 |
| Glycerol | 0.5 | 0.5 |
| Cetylstearyl alcohol (C16/C18 30/70 - NAFOL 1618F) | 8 | 8 |
| Oxyethylenated cetylstearyl alcohol (33 EO) | 3 | 3 |
| Oxyethylenated rapeseed acid amide (4 EO) | 1.2 | 1.2 |
| Vitamin E: DL-α-tocopherol | 0.1 | 0.1 |
| Water | Qs 100 | Qs 100 |

Mode of Application

The compositions detailed above were mixed together at the time of use in the following proportions:
  10 g of composition 1,
  4 g of composition 2,
  16 g of composition 3 or 3'.

The resulting mixture was then applied to locks of natural hair comprising 90% grey hairs, in a proportion of 10 g of mixture per 1 g of hair.

The mixture was left on the fibers at ambient temperature for 30 minutes.

The hair was then rinsed, washed with a standard shampoo and dried.

Light-chestnut locks were obtained upon visual evaluation. The hair had an excellent feel.

What is claimed is:

1. A composition for treating human keratin fibers, comprising:
  (a) at least 25% by weight of at least one fatty substance not comprising a carboxylic functional group;
  (b) at least one amphoteric polymer;
  (c) at least one basifying agent; and
  (d) hydrogen peroxide.

2. The composition according to claim 1, wherein the at least one fatty substance not comprising a carboxylic functional group is chosen from $C_6$-$C_{16}$ lower alkanes; non-silicone oils of animal, plant and synthetic origin; hydrocarbons of mineral and synthetic origin; fatty alcohols; fatty acid esters; fatty alcohol esters; non-silicone waxes; and silicones.

3. The composition according to claim 1, wherein the at least one fatty substance not comprising a carboxylic functional group is chosen from liquid compounds and pasty compounds.

4. The composition according to claim 2, wherein the at least one fatty substance not comprising a carboxylic functional group is chosen from $C_6$-$C_{16}$ lower alkanes, non-silicone oils of plant and synthetic origin, hydrocarbons of mineral and synthetic origin, fatty alcohols, fatty acid esters, and fatty alcohol esters.

5. The composition according to claim 1, wherein the at least one fatty substance not comprising a carboxylic functional group is chosen from liquid petroleum jelly, polydecenes, fatty acid esters, fatty alcohol esters, and liquid fatty alcohols.

6. The composition according to claim 1, wherein the at least one fatty substance not comprising a carboxylic functional group is present in an amount ranging from 25% to 80% by weight, relative to the weight of the composition.

7. The composition according to claim 1, wherein the at least one amphoteric polymer is chosen from:

1) polymers comprising, as monomers, at least one monomer derived from a vinyl compound bearing a carboxylic group, and at least one basic monomer derived from a substituted vinyl compound comprising at least one basic atom, chosen from:
   a) dialkyl aminoalkyl methacrylates, dialkyl aminoalkyl acrylates, dialkyl aminoalkyl methacrylamides and dialkyl aminoalkyl acrylamides;
   b) salts of trialkyl aminoalkyl methacrylates and of trialkyl aminoalkyl acrylates, salts of trialkylaminoakylmethacrylamide and of trialkylaminoalkylacrylamide;

(2) polymers comprising units deriving from:
   (a) at least one monomer chosen from acrylamides or methacrylamides which are substituted on the nitrogen with an alkyl radical comprising from 2 to 12 carbon atoms,
   b) at least one acidic comonomer comprising at least one reactive carboxylic groups,
   c) at least one basic comonomer comprising primary, secondary, tertiary and quaternary amine substituents of acrylic and methacrylic acids and the product of quaternization of dimethylaminoethyl methacrylate with dimethyl sulphate or diethyl sulphate;

(3) copolymers comprising, as monomers, at least one monomer derived from a vinyl compound bearing a carboxylic group, and at least one monomer of diallyl dialkyl ammonium salt type, wherein the alkyl groups comprise 1 to 6 carbon atoms;

(4) crosslinked and alkylated polyamino amides partially or totally deriving from polyamino amides of formula (I):

$$-[CO-R_{10}-CO-Z]- \qquad (I)$$

wherein $R_{10}$ is chosen from divalent radicals derived from saturated dicarboxylic acids, mono- and dicarboxylic aliphatic acids comprising an ethylenic double bond, esters of a $C_1$-$C_6$ alkanol, and radicals derived from the addition of any one of those acids to a bis(primary) or bis(secondary) amine; and Z is chosen from bis(primary) radicals, and mono- and bis(secondary) polyalkylene-polyamines;

(5) polymers comprising zwitterionic units of formula (III):

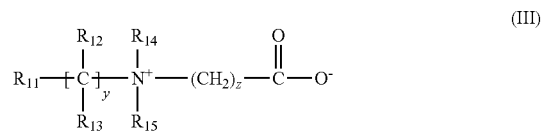

wherein $R_{11}$ is chosen from polymerizable unsaturated group, y and z are integers ranging from 1 to 3, $R_{12}$ and $R_{13}$ are chosen from a hydrogen atom, methyl, ethyl and propyl, $R_{14}$ and $R_{15}$ are chosen from a hydrogen atom and alkyl radicals such that the sum of the carbon atoms in $R_{14}$ and $R_{15}$ does not exceed 10;

(6) polymers derived from chitosan comprising monomer units chosen from those of formulae (D)-(F):

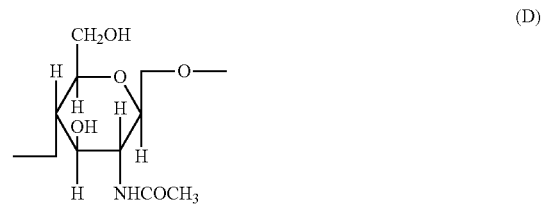

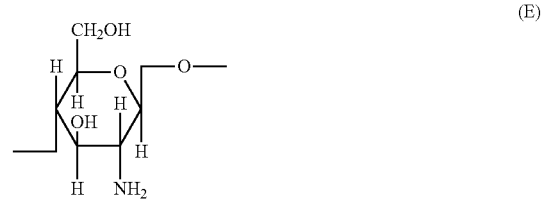

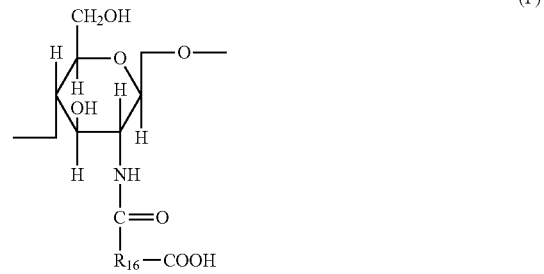

wherein the D unit is present in an amount ranging from 0% to 30%, the E unit is present in an amount ranging from 5% to 50% and the F unit is present in an amount ranging from 30% to 90%, it being understood that, in this F unit, $R_{16}$ is chosen from radicals of formula:

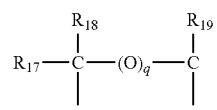

wherein, if q=0, $R_{17}$, $R_{18}$ and $R_{19}$ are each independently chosen from a hydrogen atom, methyl, hydroxyl, acetoxy, amino residues, monoalkylamine residues, and dialkylamine residues, which are optionally interrupted with at least one nitrogen atom, and/or optionally substituted with at least one group chosen from amine, hydroxyl, carboxyl, alkylthio and sulphonic groups, and alkylthio residues wherein the alkyl group bears an amino residue, and wherein at least one of the radicals $R_{17}$, $R_{18}$ and $R_{19}$ is a hydrogen atom;

or in the alternative, if q=1, $R_{17}$, $R_{18}$ and $R_{19}$ are each independently chosen from a hydrogen atom, and the salts formed by these compounds with bases or acids;

(7) polymers derived from the N-carboxyalkylation of chitosan;

(8) polymers having units chosen from those of formula (IV):

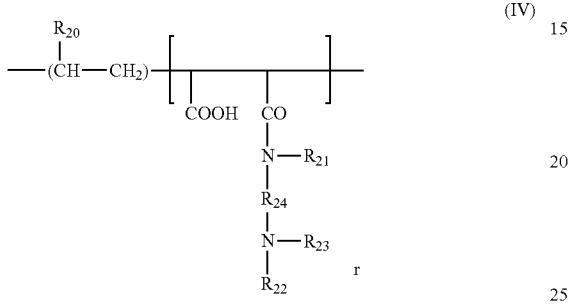

wherein $R_{20}$ is chosen from a hydrogen atom, $CH_3O$, $CH_3CH_2O$ and phenyl radicals, $R_{21}$ is chosen from a hydrogen atom and lower alkyl radicals, $R_{22}$ is a hydrogen atom and lower alkyl radicals, $R_{23}$ is chosen from lower alkyl radicals and radicals corresponding to the formula: $-R_{24}-N(R_{22})_2$, wherein $R_{24}$ is chosen from $-CH_2-CH_2-$, $-CH_2-CH_2-CH_2-$ and $-CH_2-CH(CH_3)-$, and $R_{22}$ is as defined above, and also the higher homologues of these radicals, comprising up to 6 carbon atoms;

(9) amphoteric polymers of the -D-X-D-X type chosen from:

a) polymers obtained by the action of chloroacetic acid or sodium chloroacetate on compounds comprising at least one unit of formula (V):

-D-X-D-X-D- (V)

wherein D is a radical

and X is chosen from E and E', wherein E or E' are each independently chosen from straight-chained and branched-chained, unsubstituted and substituted alkylene radicals comprising up to 7 carbon atoms in the main chain, and which optionally comprise, at least one entity chosen from oxygen, nitrogen and sulphur atoms, and 1 to 3 aromatic and/or heterocyclic rings; wherein the oxygen, nitrogen and sulphur atoms are present in the form of ether, thioether, sulphoxide, sulphone, sulphonium, alkylamine, or alkenylamine groups, or hydroxyl, benzylamine, amine oxide, quaternary ammonium, amide, imide, alcohol, ester and/or urethane groups;

b) polymers of formula (VI):

-D-X-D-X— (VI)

where D is a radical

and X is chosen from E and E', and at least once E'; wherein E is as defined above and E' is chosen from straight-chained and branched-chained alkylene radicals comprising up to 7 carbon atoms in the main chain, which is unsubstituted or substituted with at least one hydroxyl radical, and comprising at least one nitrogen atom, wherein the nitrogen atom is substituted with an alkyl chain optionally interrupted with an oxygen atom and comprising at least one carboxyl functional group or at least one hydroxyl functional group and betainized by reaction with chloroacetic acid or sodium chloroacetate; and

(10) $(C_1-C_5)$alkyl vinyl ether/maleic anhydride copolymers partially modified by semiamidation with an N,N-dialkylaminoalkylamine or by semiesterification with an N,N-dialkanolamine.

8. The composition according to claim 7, wherein the at least one amphoteric polymer is chosen from polymers defined in groups (1) to (3).

9. The composition according to claim 7, wherein the at least one amphoteric polymer is chosen from acrylic acid/acrylamidopropyltrimethylammonium chloride copolymers, acrylic acid/acrylamidopropyltrimethylammonium chloride/acrylamide copolymers, and copolymers comprising, as monomers, dimethyldiallylammonium chloride and acrylic acid optionally combined with acrylamide.

10. The composition according to claim 9, wherein the at least one amphoteric polymer is chosen from acrylic acid/acrylamidopropyltrimethylammonium chloride copolymers.

11. The composition according to claim 1, wherein the at least one amphoteric polymer is present in an amount ranging from 0.005% to 10%, by weight, relative to the total weight of the composition.

12. The composition according to claim 1, further comprising at least one oxidation dye.

13. The composition according to claim 12, wherein the at least one oxidation dye is an oxidation base chosen from para-phenylenediamines, bisphenylalkylenediamines, para-aminophenols, ortho-aminophenols, heterocyclic bases and addition salts thereof.

14. The composition according to claim 1, further comprising at least one direct dye chosen from ionic, nonionic, azo, methine, carbonyl, azine, nitro(hetero)aryl and tri(hetero)arylmethane dyes, porphyrins, phthalocyanines and natural direct dyes.

15. The composition according to claim 1, further comprising at least one compound chosen from basifying agents, inorganic alkaline, organic alkaline agents, and hybrid alkaline agents.

16. The composition according to claim 15, wherein the organic alkaline agents are organic amines chosen from alkanolamines and basic amino acids.

17. A process for dyeing or lightening human keratin fibers, comprising applying to keratin fibers at least one composition comprising:
(a) at least 25% by weight of at least one fatty substance not comprising a carboxylic functional group;
(b) at least one amphoteric polymer;

(c) at least one basifying agent; and
(d) hydrogen peroxide.

18. A multi-compartment kit for dyeing or lightening human keratin fibers comprising,
at least one first compartment comprising, at least one first composition comprising at least one fatty substance, at least one basifying agent and, optionally, at least one dye chosen from oxidation dyes and direct dyes; and
at least one second compartment comprising at least one second composition comprising at least one oxidizing agent; wherein at least one of the first and/or the second composition(s) further comprise at least one amphoteric polymer; and wherein the compositions of the compartments are intended to be mixed so as to give a composition comprising
a) at least 25% by weight of at least one fatty substance not comprising a carboxylic functional group;
(b) at least one amphoteric polymer;
(c) at least one basifying agent; and
(d) hydrogen peroxide;
just before application to the human keratin fibers.

19. A multi-compartment kit for dyeing or lightening human keratin fibers comprising,
at least one compartment comprising at least one first composition comprising at least one fatty substance;
at least one compartment comprising at least one second composition comprising at least one basifying agent and, optionally, at least one dye chosen from oxidation dyes and direct dyes; and
at least one compartment comprising at least one third composition comprising at least one oxidizing agent; wherein at least one of the first and/or the second and/or the third composition further comprise at least one amphoteric polymer; and wherein the compositions of the compartments are intended to be mixed so as to give a composition comprising
a) at least 25% by weight of at least one fatty substance not comprising a carboxylic functional group;
(b) at least one amphoteric polymer;
(c) at least one basifying agent; and
(d) hydrogen peroxide,
just before application to the human keratin fibers.

20. The composition according to claim 3, wherein the at least one fatty substance not comprising a carboxylic functional group is chosen from compounds that are liquid at ambient temperature and at atmospheric pressure.

21. The composition according to claim 6, wherein the at least one fatty substance not comprising a carboxylic functional group is present in an amount ranging from 25% to 65% by weight, relative to the weight of the composition.

22. The composition according to claim 21, wherein the at least one fatty substance not comprising a carboxylic functional group is present in an amount ranging from 30% to 55% by weight, relative to the weight of the composition.

23. The composition according to claim 11, wherein the at least one amphoteric polymer is present in an amount ranging from 0.05% to 5%, by weight, relative to the total weight of the composition.

24. The composition according to claim 23, wherein the at least one amphoteric polymer is present in an amount ranging 0.1% to 2% by weight, relative to the total weight of the composition.

25. The composition according to claim 1, further comprising at least one coupler chosen from meta-phenylenediamines, meta-aminophenols, meta-diphenols, naphthalene couplers, heterocyclic couplers and addition salts thereof.

26. The composition according to claim 15, wherein the organic alkaline agents are chosen from organic amines having a pKb at 25° C. less than 6.

27. The composition according to claim 15, wherein the hybrid alkaline agents are chosen from salts of organic amines having a pKb at 25° C. less than 12 with acids chosen from carbonic acid and hydrochloric acid.

28. The composition according to claim 7, wherein the carboxylic acid in polymers (1) and (3) is chosen from acrylic acid, methacrylic acid, maleic acid and α-chloroacrylic acid.

29. The composition according to claim 7, wherein the at least one reactive carboxylic acid in the at least one acidic comonomer in the polymer (2) is chosen from acrylic acid, methacrylic acid, crotonic acid, itaconic acid, maleic acid and fumaric acid, and $C_1$-$C_4$ alkyl monoesters of maleic and fumaric acids and anhydrides.

30. The composition according to claim 7, wherein the polymer (4) is chosen from the following polymers:
a) in proportions ranging from 60 to 100 mol %, the radical:

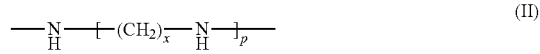

(II)

wherein x=2 and p=2 or 3, or in the alternative x=3 and p=2 this radical derived from diethylenetriamine, triethylenetetraamine or from dipropylenetriamine;
b) in proportions ranging from 0 to 40 mol %, the radical (II) above wherein x=2 and p=1 and which derives from ethylenediamine, or the radical derived from piperazine:

c) in proportions ranging from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide, and alkylated by the action of acrylic acid, chloroacetic acid or an alkane sultone, or salts thereof.

31. The composition according to claim 7, wherein the polymerizable unsaturated group in polymer (4) is chosen from an acrylate, methacrylate, acrylamide and methacrylamide groups.

* * * * *

UNITED STATES PATENT AND TRADEMARK OFFICE
CERTIFICATE OF CORRECTION

PATENT NO. : 8,118,884 B2
APPLICATION NO. : 12/976124
DATED : February 21, 2012
INVENTOR(S) : Jean-Marc Ascione and Jane Cotteret Page 1 of 1

It is certified that error appears in the above-identified patent and that said Letters Patent is hereby corrected as shown below:

Claim 7, col. 39, ll. 15-25, please replace Figure (IV) as shown below:

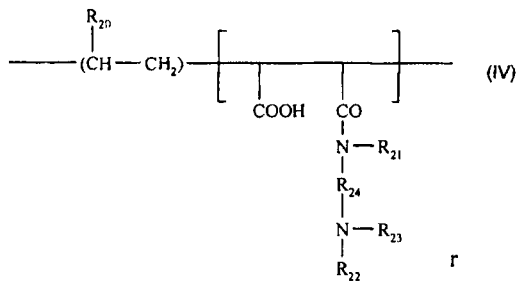

with the following Figure (IV):

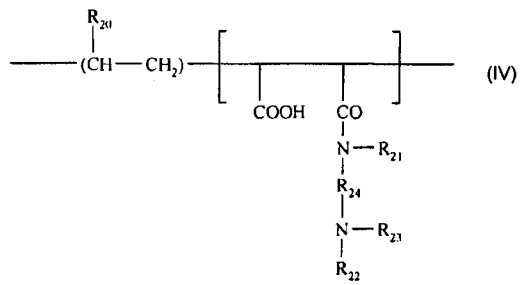

Signed and Sealed this
Eighth Day of May, 2012

David J. Kappos
*Director of the United States Patent and Trademark Office*